(12) United States Patent
Dershem et al.

(10) Patent No.: US 6,946,523 B2
(45) Date of Patent: Sep. 20, 2005

(54) HETEROBIFUNCTIONAL MONOMERS AND USES THEREFOR

(75) Inventors: Stephen M. Dershem, San Diego, CA (US); Kevin J. Forrestal, Poway, CA (US); Puwei Liu, San Diego, CA (US)

(73) Assignee: Henkel Corporation, Rocky Hill, CT (US)

( * ) Notice: Subject to any disclaimer, the term of this patent is extended or adjusted under 35 U.S.C. 154(b) by 23 days.

(21) Appl. No.: 10/612,545

(22) Filed: Jul. 1, 2003

(65) Prior Publication Data

US 2004/0082724 A1 Apr. 29, 2004

Related U.S. Application Data

(60) Continuation-in-part of application No. 10/202,427, filed on Jul. 22, 2002, now abandoned, which is a division of application No. 09/779,396, filed on Feb. 7, 2001, now Pat. No. 6,423,780.

(51) Int. Cl.⁷ ..................... C08F 32/04; C08F 232/04; C07C 207/00
(52) U.S. Cl. ................ 525/216; 525/218; 525/282; 526/262; 526/282; 526/284; 526/281; 526/308; 526/309; 562/435
(58) Field of Search .................. 525/216, 218, 525/282; 526/262, 281, 282, 284, 308, 309, 283

(56) References Cited

U.S. PATENT DOCUMENTS

| | | | |
|---|---|---|---|
| 2,882,279 A | 4/1959 | Luvisi et al. | 260/348 |
| 3,494,897 A | 2/1970 | Reding et al. | 260/78.5 |
| 3,959,234 A | 5/1976 | Kurosawa et al. | 260/78 |
| 4,080,491 A | 3/1978 | Kobayashi et al. | 526/137 |
| 4,500,687 A | 2/1985 | Wolfe | 525/412 |
| 5,188,903 A | 2/1993 | Liao et al. | 428/447 |
| 5,212,043 A | 5/1993 | Yamamoto et al. | 430/192 |
| 5,422,409 A | 6/1995 | Brekner et al. | 526/281 |
| 6,369,181 B1 * | 4/2002 | Jumg et al. | 526/271 |
| 6,423,780 B1 * | 7/2002 | Dershem et al. | 525/216 |

FOREIGN PATENT DOCUMENTS

| | | |
|---|---|---|
| DE | 40 40 995 A1 | 6/1992 |
| EP | 0 388 028 A | 9/1990 |
| EP | 0 931 816 A1 | 7/1999 |
| GB | 2 336 846 A | 11/1999 |
| JP | 02028150 * | 1/1990 |
| JP | 02029405 * | 1/1990 |
| JP | 02 029410 | 1/1990 |
| JP | 04368358 * | 4/1992 |
| JP | 05-117253 | 5/1993 |
| JP | 05230018 * | 9/1993 |
| WO | WO 00/20472 | 4/2000 |

* cited by examiner

*Primary Examiner*—James J. Seidleck
*Assistant Examiner*—Olga Asinovsky
(74) *Attorney, Agent, or Firm*—Steven C. Bauman

(57) ABSTRACT

In accordance with the present invention, there are provided novel heterobifunctional monomers and users for the same. Invention compounds have many of the properties required by the microelectronics industry, such as, for example, hydrophobicity, high $T_g$ values, low dielectric constant, ionic purity, low coefficient of thermal expansion (CTE), and the like. These properties result in a thermoset that is particularly well suited to high performance applications where typical operating temperatures are often significantly higher than those at which prior art materials were suitable. Invention compounds are particularly ideal for use in the manufacture of electronic components, such as, for example, printed circuit boards, and the like.

41 Claims, No Drawings

HETEROBIFUNCTIONAL MONOMERS AND USES THEREFOR

RELATED APPLICATIONS

This application is a continuation-in-part of U.S. patent application Ser. No. 10/202,427, filed Jul. 22, 2002 now abandoned, which is a divisional of U.S. patent application Ser. No. 09/779,396, filed Feb. 7, 2001, now U.S. Pat. No. 6,423,780, the entire contents of each of which are hereby incorporated by reference herein.

FIELD OF THE INVENTION

The present invention relates to novel heterobifunctional monomers useful in a variety of applications related to the preparation of components employed in the electronics industry. In a particular aspect, the present invention relates to formulations useful for the preparation of laminates. In another aspect, the present invention relates to formulations useful for the preparation of solder masks. In yet another aspect, the present invention relates to formulations useful for the preparation of liquid encapsulant for electronic components. In still another aspect, the present invention relates to formulations useful for the preparation of non-hermetic electronic packages.

BACKGROUND OF THE INVENTION

As the electronics industry advances, and production of light weight components increases, the development of new materials gives producers increased options for further improving the performance and ease of manufacture of such components. Materials used in the manufacture of electronic components include the resin required for the preparation of prepregs (which are, in turn, used for the preparation of multilayered printed circuit boards and printed wiring boards), resins used for the preparation of solder masks (which define solder areas on the multilayered printed wiring board), and resins used for preparation of glob top (which protects microelectronic devices from the environment).

Multilayered printed circuit boards are currently produced mainly by (a) a mass laminating technique and (b) a pin laminating technique. In these techniques, a printed circuit board for inner layer use (hereinafter, referred to as "inner-layer board") is first manufactured. This inner-layer board is combined with prepregs and then a copper foil or a single-side copper-clad laminate and the superimposed laminating materials are laminated to give a multilayered board, both sides of which are covered by a copper coating. This multilayered structure is processed as appropriate to form through-holes, outer-layer printed circuits, etc.

The initial manufacture of resins used in laminates is usually conducted by chemical producers and supplied to the trade in a workable form. Addition of a curing agent or catalyst, as well as optional components such as diluents, flow promoters, fire retardants, and other modifying resins is typically performed by the user. This may be done in the interest of customization to the application or to ensure that pre-reaction of the formulation does not occur.

Another common use of resins in the electronics industry is for the preparation of solder masks. Solder mask is used to prevent excessive flow of solder in plastic packages. The material used must maintain the integrity of the physical, chemical, mechanical, and environmentally related properties of the package. Solder masks were originally intended to be used on printed wiring boards (PWBs) as an aid to manufacturing, reducing the need for touch-up after machine soldering, reducing solder consumption, and providing mechanical protection for the main portion of the circuitry.

The main type of solder mask employed in the art is the "liquid photoimageable" solder mask. There are three primary methods of applying this type of soldermask: flood screen-coating, curtain, and spray coating. Each method has both advantages and drawbacks. Screen coating, for example, is efficient in material usage, but through-holes may be plugged in the process. These holes must then be vacated during development. Curtain coating is also efficient, but it is a much slower process since only one side of a board can be coated at a time. Spray coating is the best method to accomplish complete fill and trace application, but this technique can result in substantial material losses (e.g., in the range of 10–30% waste).

Another common use of resins in the electronics industry is as a liquid encapsulant (also referred to as "glob top"), wherein an aliquot of resin material is used to encase a component to protect it from certain stresses and from exposure to the environment. To meet the industry's ever-increasing demand for device reliability, materials for encapsulant applications must meet increasingly stringent performance requirements. Such requirements include excellent moisture resistance, ionic purity, low dielectric constant and good thermal properties. In the absence of these properties, especially in the presence of moisture and ionic impurities, corrosion (and ultimately failure of the device) will likely occur.

Yet another common use of resins in the electronics industry is in the preparation of non-hermetic electronic packages. Examples of such packages are ball grid array (BGA) assemblies, super ball grid arrays, IC memory cards, chip carriers, hybrid circuits, chip-on-board, multi-chip modules, pin grid arrays, and the like. In these structures, moisture resistance is an important consideration, both in terms of handling during assembly and reliability of the finished part. For example, absorption of moisture during assembly frequently leads to "popcorning" (the release, sometimes violent, of absorbed moisture upon heating to solder reflow temperatures). The development of moisture resistant resins for use in the preparation of non-hermetic electronic packages would be of great benefit to the art.

For all these applications, the microelectronics industry continues to require new resins which are able to meet its varying demands. Accordingly, there is a need for the development of materials to address the requirements of this rapidly evolving industry.

SUMMARY OF THE INVENTION

In accordance with the present invention, there are provided novel heterobifunctional monomers and thermoset materials derived therefrom. Invention compounds have many of the properties required by the microelectronics industry, such as, for example, hydrophobicity, high $T_g$ values, low dielectric constant, ionic purity, low coefficient of thermal expansion ("CTE"), and the like. These properties result in a thermoset that is particularly well suited to high performance applications where typical operating temperatures are often significantly higher than those at which prior art materials were suitable. Invention compounds are particularly useful in the manufacture of electronic components, such as, for example, printed circuit boards, and the like.

DETAILED DESCRIPTION OF THE INVENTION

In accordance with the present invention, there are provided heterobifunctional monomers having structure (I) as follows:

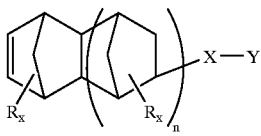

(I)

wherein:
each R is independently lower alkyl, —Br, or —I,
X is an optional bridging group,
Y is a maleimide, a nadimide, an itaconimide, an epoxy, a cyanate ester-substituted aryl, a propargyl-substituted aryl, an ethynyl-substituted aryl, a (meth)acrylate, an unsaturated anhydride, a vinyl ether, a vinyl ester, a divinyl compound, an allyl amide, a styrene, an oxazoline, or a benzoxazine,
n is 0 to about 8, and
each x is independently 0, 1 or 2.

As will be readily recognized by those of skill in the art, the bridging group X, when present, may be any one of a number of suitable spacers, depending on the desired final properties of the monomer. In some embodiments, X is a polyvalent radical selected from the group consisting of hydrocarbylene, substituted hydrocarbylene, heteroatom-containing hydrocarbylene, substituted heteroatom-containing hydrocarbylene, polysiloxane, polysiloxane-polyurethane block copolymer, and combinations of two or more thereof, optionally containing one or more linkers selected from the group consisting of a covalent bond, —O—, —S—, —NR—, —O—C(O)—, —O—C(O)—O—, —O—C(O)—NR—, —NR—C(O)—, —NR—C(O)—O—, —NR—C(O)—NR—, —S—C(O)—, —S—C(O)—O—, —S—C(O)—NR—, —S(O)—, —S(O)$_2$—, —O—S(O)$_2$—, —O—S(O)$_2$—O—, —O—S(O)$_2$—NR—, —O—S(O)—, —O—S(O)—O—, —O—S(O)—NR—, —O—NR—C(O)—, —O—NR—C(O)—O—, —O—NR—C(O)—NR—, —NR—O—C(O)—, —NR—O—C(O)—O—, —NR—O—C(O)—NR—, —O—NR—C(S)—, —O—NR—C(S)—O—, —O—NR—C(S)—NR—, —NR—O—C(S)—, —NR—O—C(S)—O—, —NR—O—C(S)—NR—, —O—C(S)—, —O—C(S)—O—, —O—C(S)—NR—, —NR—C(S)—, —NR—C(S)—O—, —NR—C(S)—NR—, —S—S(O)$_2$—, —S—S(O)$_2$—O—, —S—S(O)$_2$—NR—, —NR—O—S(O)—, —NR—O—S(O)—O—, —NR—O—S(O)—NR—, —NR—O—S(O)$_2$—, —NR—O—S(O)$_2$—O—, —NR—O—S(O)$_2$—NR—, —O—NR-S(O)—, —O—NR—S(O)—O—, —O—NR—S(O)—NR—, —O—NR—S(O)$_2$—O—, —O—NR—S(O)$_2$—NR—, —O—NR—S(O)$_2$—, —O—P(O)R$_2$—, —S—P(O)R$_2$—, —NR—P(O)R$_2$—, wherein each R is independently hydrogen, alkyl or substituted alkyl, and combinations of any two or more thereof. Preferably, X is divalent.

As employed herein, "hydrocarbylene" refers to divalent straight or branched chain hydrocarbyl groups including alkylene groups, alkenylene groups, alkynylene groups, cycloalkylene groups, heterocycloalkylene groups, arylene groups, heteroarylene groups, alkylarylene groups, arylalkylene groups, arylalkenylene groups, arylalkynylene groups, alkenylarylene groups, alkynylarylene groups, and the like; and "substituted hydrocarbylene" refers to hydrocarbylene groups further bearing one or more substituents as set forth below for substituted hydrocarbyl.

As employed herein, "hydrocarbyl" comprises any organic radical wherein the backbone thereof comprises carbon and hydrogen only. Thus, hydrocarbyl embraces alkyl, cycloalkyl, alkenyl, cycloalkenyl, alkynyl, aryl, alkylaryl, arylalkyl, arylalkenyl, alkenylaryl, arylalkynyl, alkynylaryl, and the like.

As employed herein, "substituted hydrocarbyl" comprises any of the above-referenced hydrocarbyl groups further bearing one or more substituents selected from hydroxy, alkoxy (of a lower alkyl group), mercapto (of a lower alkyl group), cycloalkyl, substituted cycloalkyl, heterocyclic, substituted heterocyclic, aryl, substituted aryl, heteroaryl, substituted heteroaryl, aryloxy, substituted aryloxy, halogen, trifluoromethyl, cyano, nitro, nitrone, amino, amido, —C(O)H, acyl, oxyacyl, carboxyl, carbamate, dithiocarbamoyl, sulfonyl, sulfonamide, sulfuryl, and the like.

As employed herein, "alkylene" refers to saturated, divalent straight or branched chain hydrocarbyl groups typically having in the range of about 2 up to about 500 carbon atoms, and "substituted alkylene" refers to alkylene groups further bearing one or more substituents as set forth above.

As employed herein, "alkenylene" refers to divalent straight or branched chain hydrocarbyl groups having at least one carbon-carbon double bond, and typically having in the range of about 2 up to 500 carbon atoms, and "substituted alkenylene" refers to alkenylene groups further bearing one or more substituents as set forth above.

As employed herein, "alkynylene" refers to divalent straight or branched chain hydrocarbyl groups having at least one carbon-carbon triple bond, and typically having in the range of about 2 up to 500 carbon atoms, and "substituted alkynylene" refers to alkynylene groups further bearing one or more substituents as set forth above.

As employed herein, "cycloalkylene" refers to divalent ring-containing groups containing in the range of about 3 up to about 8 carbon atoms, and "substituted cycloalkylene" refers to cycloalkylene groups further bearing one or more substituents as set forth above.

As employed herein, "heterocycloalkylene" refers to divalent cyclic (i.e., ring-containing) groups containing one or more heteroatoms (e.g., N, O, S, or the like) as part of the ring structure, and having in the range of 3 up to 14 carbon atoms and "substituted heterocycloalkylene" refers to heterocycloalkylene groups further bearing one or more substituents as set forth above.

As employed herein, "cycloalkenylene" refers to divalent ring-containing groups containing in the range of about 3 up to about 8 carbon atoms and having at least one carbon-carbon double bond, and "substituted cycloalkenylene" refers to cycloalkenylene groups further bearing one or more substituents as set forth above.

As employed herein, "arylene" refers to divalent aromatic groups typically having in the range of 6 up to 14 carbon atoms and "substituted arylene" refers to arylene groups further bearing one or more substituents as set forth above.

As employed herein, "alkylarylene" refers to alkyl-substituted divalent aryl groups typically having in the range of about 7 up to 16 carbon atoms and "substituted alkylarylene" refers to alkylarylene groups further bearing one or more substituents as set forth above.

As employed herein, "arylalkylene" refers to aryl-substituted divalent alkyl groups typically having in the range of about 7 up to 16 carbon atoms and "substituted arylalkylene" refers to arylalkylene groups further bearing one or more substituents as set forth above.

As employed herein, "arylalkenylene" refers to aryl-substituted divalent alkenyl groups typically having in the range of about 8 up to 16 carbon atoms and "substituted arylalkenylene" refers to arylalkenylene-groups further bearing one or more substituents as set forth above.

As employed herein, "arylalkynylene" refers to aryl-substituted divalent alkynyl groups typically having in the range of about 8 up to 16 carbon atoms and "substituted arylalkynylene" refers to arylalkynylene group further bearing one or more substituents as set forth above.

As employed herein, "alkenylarylene" refers to alkenyl-substituted divalent aryl groups typically having in the range of about 7 up to 16 carbon atoms and "substituted alkenylarylene" refers to alkenylarylene groups further bearing one or more substituents as set forth above.

As employed herein, "alkynylarylene" refers to alkynyl-substituted divalent aryl groups typically having in the range of about 7 up to 16 carbon atoms and "substituted alkynylarylene" refers to alkynylarylene groups further bearing one or more substituents as set forth above.

As employed herein, "heteroarylene" refers to divalent aromatic groups containing one or more heteroatoms (e.g., N, O, S or the like) as part of the aromatic ring, and typically having in the range of 3 up to 14 carbon atoms and "substituted heteroarylene" refers to heteroarylene groups further bearing one or more substituents as set forth above.

As employed herein, "polysiloxane-polyurethane block copolymers" refer to polymers containing both at least one polysiloxane (soft) block and at least one polyurethane (hard) block.

Preferred X groups contemplated for use in the practice of the present invention include alkylenes or oxyalkylenes comprising up to about 20 carbon atoms (typically from 2 up to about 20 carbon atoms), arylenes, siloxanes, and the like. More preferred bridging groups include alkylenes, and in particular, $C_1$–$C_6$ alkylenes. In other such embodiments, X is a $C_2$–$C_6$ alkylene.

Similarly, the Y groups indicated in structure (I) will vary according to the desired properties of the resulting monomers. Functional groups defined by Y include the unsaturated anhydrides, (meth)acrylates, styrenes, cyanate esters, vinyl ethers, vinyl esters and divinyl compounds described as free-radical curing monomers in U.S. patent application Ser. No. 10/353,774, herein incorporated by reference in its entirety. Preferred functional groups defined by Y include maleimide, nadimide, itaconimide, epoxy, cyanate ester-substituted aryl, oxazoline, and benzoxazine. When Y is an epoxy, preferred epoxy groups include alkyl epoxy, alkenyl epoxy, and alkoxy epoxy such as 2,3-epoxypropylene, 2,3epoxypropoxymethylene, and the like. Presently preferred Y groups are optionally substituted maleimide, nadimide, and itaconimide moieties. Substituents contemplated for use with maleimide, nadimide, and itaconimide Y groups include independently selected lower alkyls, halogens, and the like. Preferred substituents contemplated for use with maleimide, nadimide, and itaconimide Y groups include methyl and —Br.

Examples of heterobifunctional monomers embraced by structure (I) include those having structures II–VIII as follows:

(II)

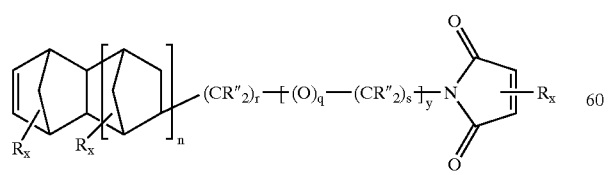

wherein:
n, R and x are as defined above,
each R" is independently hydrogen, lower alkyl, or aryl,
y is 0 up to 20,
q is 0 or 1,
r is 0 up to about 10, and
s is 0 up to about 10;

(III)

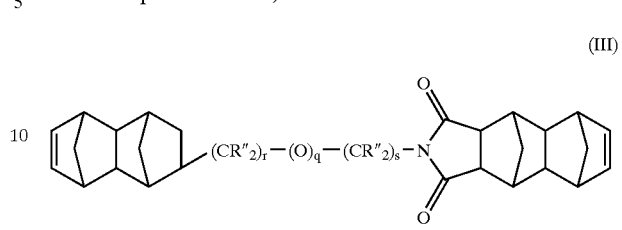

wherein:
p is 0 to 15, and
n, R, R", x, y, q, r and s are as defined above;

(IV)

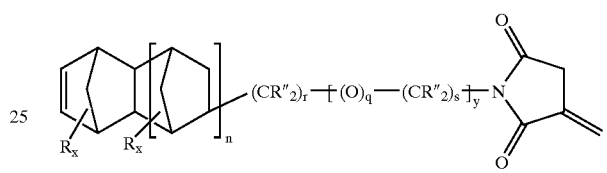

wherein:
n, R, R", x, y, q, r and s are as defined above;

(V)

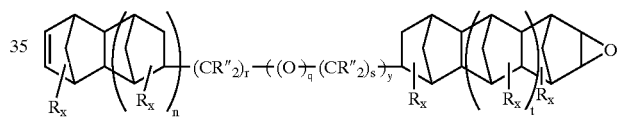

wherein:
t is 0 up to about 8,
n, R, R", x, y, q, r, and s are as defined above;

(VI)

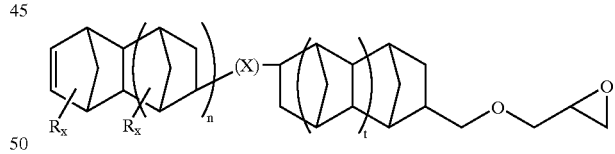

wherein:
X is an optional bridging group, and
n, t, R, and x are as defined above;

(VII)

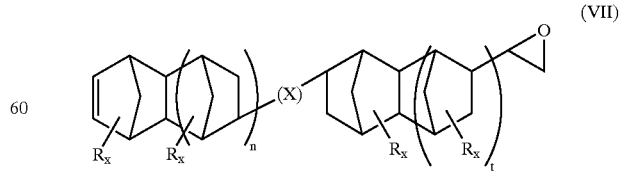

wherein:
X is an optional bridging group, and
n, t, R, and x are as defined above;

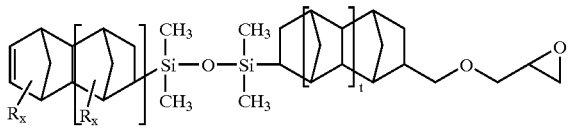

(VIII)

wherein:

n, t, R, and x are as defined above.

In another embodiment of the present invention, there are provided polymers of the above described heterobifunctional monomers. Because invention monomers are heterobifunctional, those of skill in the art will readily recognize that a wide variety of types of polymers can be generated by varying the reaction conditions, the nature of the pendant functional group Y, optional presence of comonomers, and the like. For example, the double bond functional group of the norbornyl moiety of invention monomers (hereinafter the "head") can be polymerized with the double bond functional group of other invention monomers (i.e., head-to-head polymers), the Y group functionalities (hereinafter the "tail") can be polymerized with one another (i.e., tail-to-tail polymers), the norbornyl functionalities can be polymerized with the Y group functionalities (i.e., head-to-tail polymers), and combinations thereof. For example, a polymer could be prepared with blocks of head-to-head, linked to blocks of tail-to-tail, blocks of head-to-tail, and the like.

Of course, comonomers may be included in block co-polymers described above as well. For example, blocks of comonomers can be prepared and interspersed between blocks of invention monomers. Alternatively, comonomers may participate randomly in the preparation of polymers according to the present invention. In another embodiment, comonomers can alternate with invention monomers in a first orientation to form a first block, while interacting in a second orientation to form a second block, and so forth. Thus, a block copolymer comprising any possible combination of linkages between invention monomers and one or more comonomers is contemplated as falling within the scope of the present invention.

In a further embodiment of the present invention, there are provided polymers having the structure (IX) as follows:

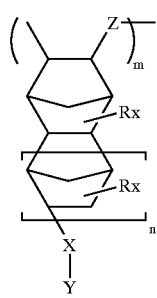

(IX)

wherein:

each R is independently lower alkyl, —Br, or —I,

X is an optional bridging group,

Y is a maleimide, a nadimide, an itaconimide, an epoxy, a cyanate ester-substituted aryl, a propargyl-substituted aryl, an ethynyl-substituted aryl, a (meth)acrylate, an unsaturated anhydride, a vinyl ether, a divinyl compound, an allyl amide, a styrene, an oxazoline, or a benzoxazine, each Z is optionally present, and when present, is independently derived from any cationically polymerizable monomer, any free-radically polymerizable monomer, or any coordinatively polymerizable monomer, m is in the range of about 3 up to about 10,000, n is 0 to about 8, and x is 0 up to 2.

Similarly, in another embodiment of the present invention, there are provided polymers having the structure (X) as follows:

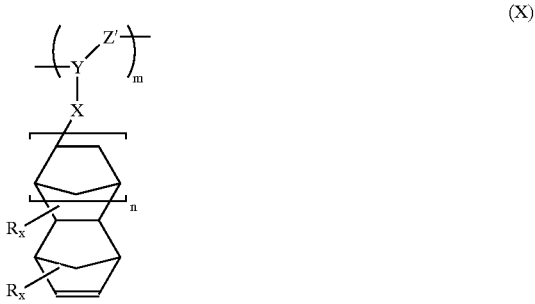

(X)

wherein:

R X, Y, n, m, and x are as defined above, each Z' is optionally present, and when present, is independently derived from any cationically polymerizable monomer, any anionically polymerizable monomer, any free-radically polymerizable monomer, or any coordinatively polymerizable monomer.

Cationically polymerizable monomers contemplated for use in the preparation of polymers having the structure (X) include styrenes, epoxies, vinyl ethers, benzoxazines, oxazolines, and the like.

Anionically polymerizable monomers contemplated for use in the preparation of polymers having the structure (X) include styrenes, maleimides, nadimides, itaconimides, (meth)acrylates, and the like.

Free-radically polymerizable monomers contemplated for use in the preparation of polymers having the structure (X) include maleimides, nadimides, itaconimides, (meth) acrylates, styrenes, vinyl esters, allyl ethers, allyl esters, and the like.

Coordinatively polymerizable monomers are monomers that may be polymerized using transition metal or other types of metal catalysts wherein the growing polymer chain is bound to a metal atom and insertion of the monomer into the metal-bound polymer chain is preceded by putative coordination of the monomer with the metal. Coordinatively polymerizable monomers contemplated for use in the preparation of polymers having the structure (X) include α-olefins, cyanates, ethynyls, propargyls, and the like.

In some embodiments of the present invention, bridging group X in structures (IX) and (X) is an alkylene or oxyalkylene having up to about 20 carbon atoms, an arylene, or a siloxane.

Alkylenes and oxyalkylenes contemplated for use in the practice of the present invention have the structure:

—(CR"$_2$)$_r$—[(O—)$_q$—(CR"$_2$)$_s$]$_y$— wherein:

each R" is independently hydrogen, lower alkyl or aryl, r falls in the range of 0 up to about 10, s falls in the range of 1 up to about 10, q is 0 or 1, and y is 0 up to 20.

Arylenes contemplated for use in the practice of the present invention include optionally substituted phenylene, naphthylene, phenanthrylene, anthracenylene, and the like.

Siloxanes contemplated for use in the practice of the present invention include siloxanes having the structure:

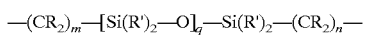

wherein:
  each R is independently defined as above,
  each R' is independently selected from hydrogen, lower alkyl or aryl,
  m' falls in the range of 0 up to 10,
  n' falls in the range of 0 up to 10, and
  q' falls in the range of 1 up to 50.

In another embodiment of the present invention, there are provided thermosetting resin compositions comprising a base formulation comprising:

(a) a heterobifunctional monomer as described herein;

(b) in the range of about 0.2 up to about 5 wt % of at least one curing catalyst, based on the total weight of the composition;

(c) optionally, at least one polycyanate ester monomer; and (d) optionally, at least one polycyclic olefin having at least one terminal norbornene functional group.

Cyanate esters contemplated for use in the practice of the present invention include those described in U.S. Pat. No. 5,789,757, the entire contents of which are incorporated by reference herein.

As readily recognized by those of skill in the art, a wide variety of curing catalysts can be employed in the preparation of invention compositions. The preferred catalyst to be used will, of course, depend on the monomer vehicle(s) employed. For example, for those monomer vehicles which cure by a free radical mechanism, free radical initiators such as peroxy esters, peroxy carbonates, hydroperoxides, alkylperoxides, arylperoxides, azo compounds, and the like can be employed.

For those monomer vehicles which cure by cationic and/or anionic polymerization, organic bases, cationic catalysts, transition metal catalysts, organic acids, and the like can be employed. Exemplary organic bases contemplated for use herein include tertiary amines (e.g., N,N-dimethyl aniline, N,N-dimethyl toluidine, N,N-dimethyl-p-anisidine, p-halogeno-N,N-dimethyl anilines, 2-N-ethyl aniline ethanol, tri-n-butyl amine, pyridine, quinoline, N-methyl morpholine, triethanolamine, and the like); imidazoles (e.g., imidazole or benzimidazole); and the like. Organic acids include phenols (e.g., phenol, cresol, xylenol, resorcinol, phloroglucin, and the like), carboxylic acids, anhydrides, and the like.

Exemplary cationic catalysts contemplated for use herein include onium salts, iodonium salts, sulfonium salts, and the like.

Exemplary metal catalysts contemplated for use herein include titanium, zirconium, hafnium, lead, zinc, tin, manganese, nickel, copper, cobalt and the like, in the form of a chelate, a soap, or the like. Examples of such compounds include metallocenes of titanium, zirconium, or hafnium, lead naphthenate, lead stearate, zinc naphthenate, tin oleate, dibutyl tin maleate, manganese naphthenate, cobalt naphthenate, lead salt of resin acid, chlorides such as $ZnCl_2$, $SnCl_4$ or $AlCl_3$, and the like.

Polycyclic olefins contemplated for optional use in thermosetting resins of the present invention include maleimides, nadimides, itaconimides, epoxies, cyanate ester-substituted aryls, propargyl-substituted aryls, ethynyl-substituted aryls, (meth)acrylates, unsaturated anhydrides, vinyl ethers, divinyl compounds, allyl amides, a styrenes, oxazolines, benzoxazines, and the like. Exemplary polycyclic olefins include those having structures (XI) and (XII) as follows:

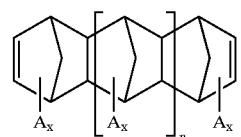

(XI)

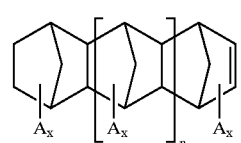

(XII)

wherein:
  each A is independently
    (a) an alkyl or substituted alkyl, or
    (b) —X'—Y',
      wherein:
        X' is an optional bridging group, and
        Y' is a maleimide, a nadimide, an itaconimide, an epoxy, a cyanate ester-substituted aryl, a propargyl-substituted aryl, an ethynyl-substituted aryl, a (meth)acrylate, an unsaturated anhydride, a vinyl ether, a divinyl compound, an allyl amide, a styrene, an oxazoline, or a benzoxazine,
  each x is independently 0, 1 or 2, and
  n is 0 to about 8.

Optional bridging groups X' contemplated for use in structures (XI) and (XII) include (oxy)alkylenes (i.e, alkylenes or oxyalkylenes) comprising up to about 20 carbon atoms.

Optionally, invention compositions can further contain one or more of the following additional components: anti-oxidants, bleed control agents, one or more fillers, inert (i.e., nonreactive) diluents, reactive diluents, coupling agents, adhesion promoters, flexibilizers, dyes, pigments, and the like.

Anti-oxidants contemplated for use in the practice of the present invention include hindered phenols (e.g., BHT (butylated hydroxytoluene), BHA (butylated hydroxyanisole), TBHQ (tertiary-butyl hydroquinone), 2,2'-methylenebis(6-tertiary-butyl-p-cresol), and the like), hindered amines (e.g., diphenylamine, N,N'-bis(1,4-dimethylpentyl-p-phenylene diamine, N-(4-anilinophenyl) methacrylamide, 4,4'-bis($\alpha$,$\alpha$-dimethylbenzyl) diphenylamine, and the like), phosphites, and the like. When used, the quantity of anti-oxidant typically falls in the range of about 100 up to 2000 ppm, relative to the weight of the base formulation.

Bleed control agents contemplated for use in the practice of the present invention include cationic surfactants, tertiary amines, tertiary phosphines, amphoteric surfactants, polyfunctional compounds, and the like, as well as mixtures of any two or more thereof. Those of skill in the art recognize that the quantity of bleed control agent employed in the practice of the present invention can vary widely, typically falling in the range of about 0.1 up to about 10 wt %, relative to the weight of the base formulation.

Fillers traditionally employed for the preparation of resin materials having electrically insulating properties are non-conductive materials such as, for example, aluminum nitride, boron nitride, alumina, silicon dioxide, teflon, polyolefins, and the like. Those of skill in the art readily recognize that the desirability of including filler in the invention composition will depend on the end use contemplated therefor. Thus, for example, when preparing compositions for use as a solder mask, filler is not typically employed. Conversely, when preparing compositions for use as a liquid encapsulant, it is desirable to include substantial quantities of filler therein (typically in the range of about 10 up to 75 wt % filler, relative to the weight of the base formulation).

While the use of inert diluents is not excluded from the practice of the present invention, it is generally preferred that compositions according to the invention remain substantially free of solvent, so as to avoid the potentially detrimental effects thereof, e.g., creation of voids caused by solvent escape, the environmental impact of vaporized solvent, the redeposition of outgassed molecules on the surface of the article, and the like. When used, suitable inert diluents include dimethylformamide, dimethylacetamide, N-methylpyrrolidone, toluene, xylene, methylene chloride, tetrahydrofuran, glycol ethers, methyl ethyl ketone or monoalkyl or dialkyl ethers of ethylene glycol, polyethylene glycol, propylene glycol, polypropylene glycol, and the like. When used, inert diluents are typically present in the range of about 10 up to 40 wt %, relative to the weight of the base formulation.

Reactive diluents contemplated for use in the practice of the present invention include any reactive diluent which, in combination with the maleimide-, nadimide-, and itaconimide-based formulations described herein, forms a thermosetting resin composition. Such reactive diluents include acrylates and methacrylates of monofunctional and polyfunctional alcohols, ethylenically unsaturated compounds, styrenic monomers (i.e., ethers derived from the reaction of vinyl benzyl chlorides with mono-, di-, or trifunctional hydroxy compounds), and the like. When used, reactive diluents are typically present in the range of about 5 up to 15 wt %, relative to the weight of the base formulation.

In a particular aspect, compositions according to the invention optionally further contain in the range of about 0.1 up to about 10 wt % of at least one coupling agent, based on the total weight of the composition. Coupling agents contemplated for use in the practice of the present invention include silicate esters, metal acrylate salts, titanates or compounds containing a co-polymerizable group and a chelating ligand.

Adhesion promoters contemplated for use in the practice of the present invention include polymers that have pendant acid or latent acid groups that can increase adhesion. An example is the Ricon R-130 20% maleated (Ricon Resins, Inc., Grand Junction, Colo.), a polybutadiene with anhydride groups that can react with a surface to increase adhesion. When present, adhesion promoters are typically present in the range of about 5 up to 30 wt %, relative to the weight of the base formulation.

Flexibilizers contemplated for use in the practice of the present invention include branched polyalkanes or polysiloxanes that lower the $T_g$ of the formulation. An example of such a material would be polybutadienes such as the Ricon R-130 as described hereinabove. When present, flexibilizers are typically present in the range of about 15 up to about 60 wt %, relative to the weight of the base formulation.

Dyes contemplated for use in the practice of the present invention include nigrosine, Orasol blue GN, phthalocyanines, and the like. When used, organic dyes in relatively low amounts (i.e., amounts less than about 0.2 wt %) provide contrast.

Pigments contemplated for use in the practice of the present invention include any particulate material added solely for the purpose of imparting color to the formulation, e.g., carbon black, metal oxides (e.g., $Fe_2O_3$, titanium oxide), and the like. When present, pigments are typically present in the range of about 0.5 up to about 5 wt %, relative to the weight of the base formulation.

As readily recognized by those of skill in the art, the quantity of the various components employed to prepare invention compositions can vary within wide ranges. For example, the quantity of the heterobifunctional monomer component typically falls in the range of about 10 up to 99.8 wt % of the base formulation, the quantity of polycyanate ester monomer(s) typically comprise(s) in the range of about 0 up to 89.8 wt % of the base formulation, the quantity of polycyclic olefin having at least one terminal norbornene functional group typically comprises in the range of about 0 up to 89.8 wt % of the base formulation, and the curing catalyst typically comprises in the range of about 0.2 up to about 5 wt % of the base formulation, wherein wt % in all instances is based on the total weight of all components of the base formulation.

In accordance with additional embodiments of the present invention, there are provided methods for the synthesis of the various monomers described herein. Thus, in one embodiment of the present invention, there are provided methods for synthesizing heterobifunctional monomers of structure (I), the methods comprising contacting a primary amine with a defined reactant under cyclodehydration reaction conditions, wherein the primary amine has the structure:

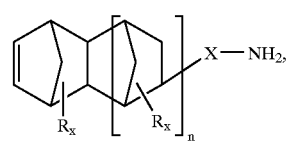

R, X, x, and n are as defined above; and the defined reactant is selected from an optionally substituted maleic anhydride, a Diels-Alder adduct of maleic anhydride and cyclopentadiene, a methylene-dihydro-furan-2,5-dione, or an epoxy.

Other monomers of the present invention may readily be prepared by techniques well-known to those of skill in the art, including, for example, hydrosilylation of olefin substituted polycyclic hydrocarbyl groups, nucleophilic addition of alkanol substituted polycyclic hydrocarbyl groups to haloalkanes, esterification of dicarboxylic acids with alkanol substituted polycyclic hydrocarbyl groups, and the like.

In another embodiment of the present invention there are provided methods for synthesizing polymers comprising a plurality of heterobifunctional monomers of structure (I), the methods comprising subjecting a plurality of the invention heterobifunctional monomers to a Zeigler-type coordinative reaction, a cationic cure, an anionic cure, a free radical ring opening or a ring-opening metathesis reaction. Such curing techniques are well known to those skilled in the art.

In another aspect of the foregoing embodiment, there are provided methods for synthesizing polymers of invention heterobifunctional monomers of structure (I), wherein the norbornyl functional groups of the heterobifunctional monomers are polymerized, the methods comprising subjecting a plurality of the above-described heterobifunctional monomers to a Zeigler-type coordinative reaction, a cationic cure, or a free radical ring opening.

In another aspect of the foregoing embodiment, there are provided methods for synthesizing polymers of invention heterobifunctional monomers of structure (I), wherein the Y functional groups of the heterobifunctional monomers are polymerized, the methods comprising subjecting a plurality of the invention heterobifunctional monomers to an anionic cure.

In another aspect of the foregoing embodiment, there are provided methods for synthesizing polymers of invention heterobifunctional monomers of structure (I), wherein alternating norbornyl functional groups of the heterobifunctional monomers are polymerized with the Y functional groups of the heterobifunctional monomers, the methods comprising subjecting a plurality of the invention heterobifunctional monomers to a free radical cure.

In another embodiment of the present invention there are provided methods for synthesizing block copolymers comprising:

(a) one or more blocks of a plurality of polymerized heterobifunctional monomers as described herein, and (b) one or more blocks of a polymerized comonomer selected from the group consisting of heterobifunctional monomers as described herein, a maleimide, a nadimide, an itaconimide, an epoxy, a cyanate ester-substituted aryl, a propargyl-substituted aryl, an ethynyl-substituted aryl, a (meth)acrylate, an unsaturated anhydride, a vinyl ether, a divinyl compound, an allyl amide, a styrene, an oxazoline, or a benzoxazine, wherein the block(s) of (a) are different from the block(s) of (b); the methods comprising (i) synthesizing a first block polymer by subjecting a first plurality of the heterobifunctional monomers to a Zeigler-type coordinative reaction, a cationic cure, or a free radical ring opening, (ii) synthesizing a second block polymer by subjecting a second plurality of heterobifunctional monomers to a free radical reaction, an anionic cure, or a UV catalyzed cationic cure, and (iii) subjecting a plurality of first and second block polymers to one or more of a Zeigler-type coordinative reaction, a cationic cure, an anionic cure or a ring-opening metathesis reaction.

Preferred molecular weights of block copolymers of this invention fall in the range of 400–10,000 or higher. Presently preferred molecular weights of such block copolymers are in the range of 500–3000.

In still another embodiment of the present invention, there are provided methods for synthesizing polymers having structure (IX), the methods comprising subjecting a plurality of monomers comprising any cationically polymerizable monomer, any free-radically polymerizable monomer, or any coordinatively polymerizable monomer, and monomers of structure (I) to one or more of a Zeigler-type coordinative reaction, a cationic cure, an anionic cure, a free radical ring opening or a ring-opening metathesis reaction.

In yet another embodiment of the present invention, there are provided methods for synthesizing polymers having structure (X), the methods comprising subjecting a plurality of monomers comprising any cationically polymerizable monomer, any free-radically polymerizable monomer, or any coordinatively polymerizable monomer, and monomers of structure (I) to one or more of a Zeigler-type coordinative reaction, a cationic cure, an anionic cure, a free radical ring opening or a ring-opening metathesis reaction.

In accordance with another embodiment of the present invention, there are provided assemblies comprising a first article permanently adhered to a second article by the adhesive properties of the base formulation described herein. Examples of the types of articles contemplated for preparation in accordance with the present invention include laminated circuit boards (i.e., the first article and the second article are separate layers of a laminate structure), printed wiring boards, and the like.

Examples of the base materials contemplated for use in the preparation of laminates include woven fabrics of various glasses such as E-glass, S-glass, SII'-glass, D-glass, quartz glass, and the like, and other inorganic woven fabrics such as alumina paper; woven fabrics made of super heat-resistant resins such as all-aromatic polyamides, polyimides, fluoroplastics, poly(phenylene sulfide), polyetheretherketones, polyetherimides, liquid-crystal polyester resins, and the like; woven fabrics obtained using composite yarns comprising combinations of fibers of the above inorganic materials and fibers of the above super heat-resistant resins; and other woven fabrics including those comprising suitable combinations of the above.

Thus, when formulations as described herein are used for the preparation of laminates, the quantity of the heterobifunctional monomer component typically falls in the range of about 15 up to about 30 wt % of the base formulation, while the quantity of polycyanate ester monomer(s) typically comprise(s) in the range of about 65 up to about 84.8 wt % of the base formulation, and the curing catalyst typically comprises in the range of about 0.2 up to about 5 wt % of the base formulation, wherein wt % in all instances is based on the total weight of all components of the base formulation.

In accordance with yet another embodiment of the present invention, there are provided articles comprising a circuit board having a solder mask deposited thereon, wherein the solder mask is prepared from compositions described herein. Solder masks are widely used in the electronics industry, and are well known to those of skill in the art. Thus, those of skill in the art can readily determine how to use the compositions described herein for such applications.

Thus, when formulations as described herein are used for the preparation of solder mask, the quantity of the maleimide, nadimide, or itaconimide component typically falls in the range of about 95 up to about 99.8 wt % of the base formulation, while polycyanate ester monomer(s) is typically not added. Curing catalyst typically falls in the range of about 0.2 up to about 5 wt % of the base formulation, wherein wt % in all instances is based on the total weight of all components of the base formulation.

In accordance with yet another embodiment of the present invention, there are provided articles comprising an electronic component encased within an aliquot of the above-described thermosetting composition. For this specific application of invention compositions, it is desirable to include filler therein in order to enhance the rheological properties thereof.

Thus, when formulations described herein are used for the preparation of a glob top, the quantity of the heterobifunctional monomer component typically falls in the range of about 15 up to about 40 wt % of the base formulation, while the quantity of polycyanate ester monomer(s) typically comprise(s) in the range of about 55 up to about 84.8 wt % of the base formulation, and the curing catalyst typically comprises in the range of about 0.2 up to about 5 wt % of the base formulation, wherein wt % in all instances is based on the total weight of all components of the base formulation.

Alternatively, when formulations described herein are used for the preparation of a glob top, a formulation based predominantly on maleimide-, nadimide-, or itaconimide-based heterobifunctional monomers can be employed, i.e., the quantity of the maleimide-, nadimide-, or itaconimide-based monomer component typically falls in the range of about 95 up to about 99 wt % of the base formulation, and the curing catalyst typically falls in the range of about 1 up to about 5 wt % of the base formulation, wherein wt. % in all instances is based on the total weight of all components of the base formulation.

Optionally, thermosetting compositions as described herein may include at least one of a maleimide, a nadimide, or an itaconimide having, respectively the formulas XIII, XIV, and XV:

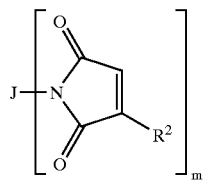

(XIII)

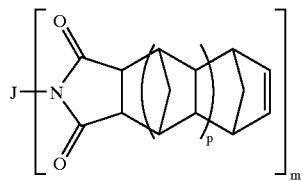

(XIV)

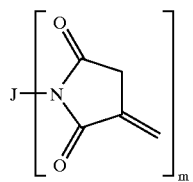

(XV)

wherein:
m=1–15,
p=0–15,
each $R^2$ is independently selected from hydrogen or lower alkyl, and
J is a monovalent or a polyvalent moiety comprising organic or organosiloxane radicals, and combinations of two or more thereof.

In one embodiment, J is a monovalent or polyvalent radical selected from the group consisting of hydrocarbyl, substituted hydrocarbyl, heteroatom-containing hydrocarbyl, substituted heteroatom-containing hydrocarbyl, hydrocarbylene, substituted hydrocarbylene, heteroatom-containing hydrocarbylene, substituted heteroatom-containing hydrocarbylene, polysiloxane, polysiloxane-polyurethane block copolymer, and combinations of two or more thereof, optionally containing one or more linkers selected from the group consisting of a covalent bond, —O—, —S—, —NR—, —O—C(O)—, —O—C(O)—O—, —O—C(O)—NR—, —NR—C(O)—, —NR—C(O)—O—, —NR—C(O)—NR—, —S—C(O)—, —S—C(O)—O—, —S—C(O)—NR—, —S(O), —S(O)$_2$—, —O—S(O)$_2$—, —O—S(O)$_2$—O—, —O—S(O)$_2$—NR—, —O—S(O)—, —O—S(O)—O—, —O—S(O)—NR—, —O—NR—C(O)—, —O—NR—C(O)—O—, —O—NR—C(O)—NR—, —NR—O—C(O)—, —NR—O—C(O)—O—, —NR—O—C(O)—NR—, —O—NR—C(S)—, —O—NR—C(S)—O—, —O—NR—C(S)—NR—, —NR—O—C(S)—, —NR—O—C(S)—O—, —NR—O—C(S)—NR—, —O—C(S)—, —O—C(S)—O—, —O—C(S)—NR—, —NR—C(S)—, —NR—C(S)—O—, —NR—C(S)—NR—, —S—S(O)$_2$—, —S—S(O)$_2$—O—, —S—S(O)$_2$—NR—, —NR—O—S(O)—, —NR—O—S(O)—O—, —NR—O—S(O)—NR—, —NR—O—S(O)$_2$—, —NR—O—S(O)$_2$—O—, —NR—O—S(O)$_2$—NR—, —O—NR—S(O)—, —O—NR—S(O)—O—, —O—NR—S(O)—NR—, —O—NR—S(O)$_2$—O—, —O—NR—S(O)$_2$—NR—, —O—NR—S(O)$_2$—, —O—P(O)R$_2$—, —S—P(O)R$_2$—, —NR—P(O)R$_2$—, wherein each R is independently hydrogen, alkyl or substituted alkyl, and combinations of any two or more thereof.

As employed herein, "alkyl" refers to saturated straight or branched chain hydrocarbon radical having in the range of 1 up to about 500 carbon atoms. "Lower alky" refers to alkyl groups having in the range of 1 up to about 5 carbon atoms. "Substituted alkyl" refers to alkyl groups further bearing one or more substituents as set forth above.

As employed herein, "alkenyl" refers to straight or branched chain hydrocarbyl groups having at least one carbon-carbon double bond, and typically having in the range of about 2 up to 500 carbon atoms, and "substituted alkenyl" refers to alkenyl groups further bearing one or more substituents as set forth above.

As employed herein, "alkynyl" refers to straight or branched chain hydrocarbyl groups having at least one carbon-carbon triple bond, and typically having in the range of about 2 up to 500 carbon atoms, and "substituted alkynyl" refers to alkynyl groups further bearing one or more substituents as set forth above.

As employed herein, "cycloalkyl" refers to a cyclic ring-containing groups containing in the range of about 3 up to about 8 carbon atoms, and "substituted cycloalkyl" refers to cycloalkyl groups further bearing one or more substituents as set forth above.

As employed herein, "cycloalkenyl" refers to cyclic ring-containing groups containing in the range of 3 up to 20 carbon atoms and having at least one carbon-carbon double bond, and "substituted cycloalkenyl" refers to cycloalkenyl groups further bearing one or more substituents as set forth above.

As employed herein, "aryl" refers to aromatic groups having in the range of 6 up to 14 carbon atoms and "substituted aryl" refers to aryl groups further bearing one or more substituents as set forth above.

As employed herein, "alkylaryl" refers to alkyl-substituted aryl groups and "substituted alkylaryl" refers to alkylaryl groups further bearing one or more substituents as set forth above.

As employed herein, "arylalkyl" refers to aryl-substituted alkyl groups and "substituted arylalkyl" refers to arylalkyl groups further bearing one or more substituents as set forth above.

As employed herein, "arylalkenyl" refers to aryl-substituted alkenyl groups and "substituted arylalkenyl" refers to arylalkenyl groups further bearing one or more substituents as set forth above.

As employed herein, "alkenylaryl" refers to alkenyl-substituted aryl groups and "substituted alkenylaryl" refers to alkenylaryl groups further bearing one or more substituents as set forth above.

As employed herein, "arylalkynyl" refers to aryl-substituted alkynyl groups and "substituted arylalkynyl" refers to arylalkynyl groups further bearing one or more substituents as set forth above.

As employed herein, "alkynylaryl" refers to alkynyl-substituted aryl groups and "substituted alkynylaryl" refers to alkynylaryl groups further bearing one or more substituents as set forth above.

As employed herein, "heterocyclic" refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above. Exemplary heterocyclic moieties include saturated rings, unsaturated rings, and aromatic heteroatom-containing ring systems, e.g., epoxy, tetrahydrofuran, oxazoline, oxazine, pyrrole, pyridine, furan, and the like.

When one or more of the above described monovalent or polyvalent groups contain one or more of the above described linkers to form the "J" appendage of a maleimide, succinimide or itaconimide group, as readily recognized by those of skill in the art, a wide variety of organic chains can be produced, such as, for example, oxyalkyl, thioalkyl, aminoalkyl, carboxyalkyl, oxyalkenyl, thioalkenyl, aminoalkenyl, carboxyalkenyl, oxyalkynyl, thioalkynyl, aminoalkynyl, carboxyalkynyl, oxycycloalkyl, thiocycloalkyl, aminocycloalkyl, carboxycycloalkyl, oxycloalkenyl, thiocycloalkenyl, aminocycloalkenyl, carboxycycloalkenyl, heterocyclic, oxyheterocyclic, thioheterocyclic, aminoheterocyclic, carboxyheterocyclic, oxyaryl, thioaryl, aminoaryl, carboxyaryl, heteroaryl, oxyheteroaryl, thioheteroaryl, aminoheteroaryl, carboxyheteroaryl, oxyalkylaryl, thioalkylaryl, aminoalkylaryl, carboxyalkylaryl, oxyarylalkyl, thioarylalkyl, aminoarylalkyl, carboxyarylalkyl, oxyarylalkenyl, thioarylalkenyl, aminoarylalkenyl, carboxyarylalkenyl, oxyalkenylaryl, thioalkenylaryl, aminoalkenylaryl, carboxyalkenylaryl, oxyarylalkynyl, thioarylalkynyl, aminoarylalkynyl, carboxyarylalkynyl, oxyalkynylaryl, thioalkynylaryl, aminoalkynylaryl or carboxyalkynylaryl, oxyalkylene, thioalkylene, aminoalkylene, carboxyalkylene, oxyalkenylene, thioalkenylene, aminoalkenylene, carboxyalkenylene, oxyalkynylene, thioalkynylene, aminoalkynylene, carboxyalkynylene, oxycycloalkylene, thiocycloalkylene, aminocycloalkylene, carboxycycloalkylene, oxycycloalkenylene, thiocycloalkenylene, aminocycloalkenylene, carboxycycloalkenylene, oxyarylene, thioarylene, aminoarylene, carboxyarylene, oxyalkylarylene, thioalkylarylene, aminoalkylarylene, carboxyalkylarylene, oxyarylalkylene, thioarylalkylene, aminoarylalkylene, carboxyarylalkylene, oxyarylalkenylene, thioarylalkenylene, aminoarylalkenylene, carboxyarylalkenylene, oxyalkenylarylene, thioalkenylarylene, aminoalkenylarylene, carboxyalkenylarylene, oxyarylalkynylene, thioarylalkynylene, aminoarylalkynylene, carboxyarylalkynylene, oxyalkynylarylene, thioalkynylarylene, aminoalkynylarylene, carboxyalkynylarylene, heteroarylene, oxyheteroarylene, thioheteroarylene, aminoheteroarylene, carboxyheteroarylene, heteroatom-containing di- or polyvalent cyclic moiety, oxyheteroatom-containing di- or polyvalent cyclic moiety, thioheteroatom-containing di- or polyvalent cyclic moiety, aminoheteroatom-containing di- or polyvalent cyclic moiety, carboxyheteroatom-containing di- or polyvalent cyclic moiety, and the like.

In another embodiment, maleimides, succinimides, and itaconimides contemplated for use in the practice of the present invention have the structures XIII, XIV, or XV, wherein, m=1–6, p=0–6, and J is (a) saturated straight chain alkyl or branched chain alkyl, optionally containing optionally substituted aryl moieties as substituents on the alkyl chain or as part of the backbone of the alkyl chain, and wherein the alkyl chains have up to about 20 carbon atoms;

(b) a siloxane having the structure: $-(C(R^3)_2)_d-[Si(R^4)_2-O]_f-Si(R^4)_2-(C(R^3)_2)_e-$, $-(C(R^3)_2)_d-C(R^3)-C(O)O-(C(R^3)_2)_d-[Si(R^4)_2-O]_f-Si(R^4)_2-(C(R^3)_2)_e-O(O)C-(C(R^3)_2)_e-$, or $-(C(R^3)_2)_d-C(R^3)-O(O)C-(C(R^3)_2)_d-[Si(R^4)_2-O]_f-Si(R^4)_2-(C(R^3)_2)_e-C(O)O-(C(R^3)_2)_e-$ wherein:

each $R^3$ is independently hydrogen, alkyl or substituted alkyl, each $R^4$ is independently hydrogen, lower alkyl or aryl, d=1–10, e=1–10, and f=1–50;

(c) a polyalkylene oxide having the structure:

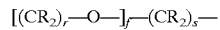

wherein:

each R is independently hydrogen, alkyl or substituted alkyl, r=1–10, s=1–10, and f is as defined above;

(d) aromatic groups having the structure:

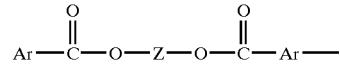

wherein each Ar is a monosubstituted, disubstituted or trisubstituted aromatic or heteroaromatic ring having in the range of 3 up to 10 carbon atoms, and Z is:

(i) saturated straight chain alkylene or branched chain alkylene, optionally containing saturated cyclic moieties as substituents on the alkylene chain or as part of the backbone of the alkylene chain, or (ii) polyalkylene oxides having the structure:

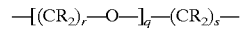

wherein each R is independently defined as above, r and s are each defined as above, and q falls in the range of 1 up to 50;

(e) di- or tri-substituted aromatic moieties having the structure:

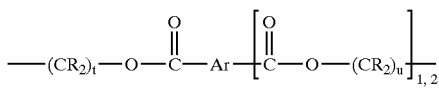

wherein each R is independently defined as above, t falls in the range of 2 up to 10, u falls in the range of 2 up to 10, and, Ar is as defined above;

(f) aromatic groups having the structure:

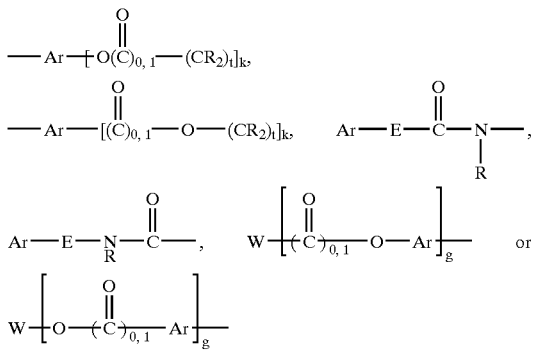

wherein:
each R is independently defined as above,
t=2–10,
k=1, 2 or 3,
g=1 up to about 50,
each Ar is as defined above,
E is —O— or —$NR^5$—, wherein $R^5$ is hydrogen or lower alkyl; and
W is
(i) straight or branched chain alkyl, alkylene, oxyalkylene, alkenyl, alkenylene, oxyalkenylene, ester, or polyester,
(ii) a siloxane having the structure —$(C(R^3)_2)_d$—[$Si(R^4)_2$—O]$_f$—$Si(R^4)_2$—$(C(R^3)_2)_e$—, —$(C(R^3)_2)_d$—$C(R^3)$—C(O)O—$(C(R^3)_2)_d$—[$Si(R^4)_2$—O]$_f$—$Si(R^4)_2$—$(C(R^3)_2)_e$—O(O)C—$(C(R^3)_2)_e$—, or —$(C(R^3)_2)_d$—$C(R^3)$—O(O)C—$(C(R^3)_2)_d$—[$Si(R^4)_2$—O]$_f$—$Si(R^4)_2$—$(C(R^3)_2)_e$—C(O)O—$(C(R^3)_2)_e$— wherein,
each $R^3$ is independently hydrogen, alkyl or substituted alkyl,
each $R^4$ is independently hydrogen, lower alkyl or aryl,
d=1–10,
e=1–10, and
f=1–50; or
(iii) a polyalkylene oxide having the structure:

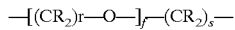

wherein:
each R is independently hydrogen, alkyl or substituted alkyl,
r=1–10,
s=1–10, and
f is as defined above;
optionally containing substituents selected from hydroxy, alkoxy, carboxy, nitrile, cycloalkyl or cycloalkenyl;

(g) a urethane group having the structure:

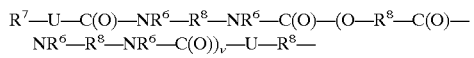

wherein:
each $R^6$ is independently hydrogen or lower alkyl;
each $R^7$ is independently an alkyl, aryl, or arylalkyl group having 1 to 18 carbon atoms;
each $R^8$ is an alkyl or alkyloxy chain having up to about 100 atoms in the chain, optionally substituted with Ar;
U is —O—, —S—, —N(R)—, or —$P(L)_{1,2}$— wherein R as defined above, and wherein each L is independently =O, =S, —OR or —R; and
v=0–50;
(h) polycyclic alkenyl; or
(i) mixtures of any two or more thereof.

In another embodiment, J is of sufficient length to render liquid the maleimide, succinimide, itaconimide or combinations of two or more thereof. In some such embodiments, m=1, 2 or 3, and J is a branched chain alkyl or alkylene, with or without substitution or interruption by one or more heteroatoms, of sufficient length and branching to render liquid the maleimide, succinimide, itaconimide or combinations of two or more thereof.

In preferred embodiments, the maleimide is N-methylmaleimide, N-ethylmaleimide, N-propylmaleimide, N-butylmaleimide, N-t-butylmaleimide, N-hexylmaleimide, N-2-ethylhexylmaleimide, N-cyclohexylmaleimide, N-octylmaleimide, N-decylmaleimide, N-dodecylmaleimide, N-phenylmaleimide, 2-methyl-N-phenylmaleimide, 4-methyl-N-phenylmaleimide, 2-ethyl-N-phenylmaleimide, 4-ethyl-N-phenylmaleimide, 2,6-diethyl-N-phenylmaleimide, and the like, or a mixture of any two or more thereof.

In accordance with another embodiment of the present invention, there are provided improved non-hermetic electronic packages, wherein the improvement comprises employing a maleimide-, nadimide-, or itaconimide-based composition as described herein for each component of the package, i.e., wherein heterobifunctional monomers according to the invention are employed for the preparation of the maleimide-, nadimide-, or itaconimide-based composition.

Those of skill in the art recognize that many different electronic packages would benefit from preparation using the hydrophobic maleimide-, nadimide-, or itaconimide-based resins described herein. Examples of such packages include ball grid arrays, super ball grid arrays, IC memory cards, chip carriers, hybrid circuits, chip-on-board, multichip modules, pin grid arrays, chip size packages (CSPs), and the like.

The invention will now be described in greater detail by reference to the following non-limiting examples.

EXAMPLE 1

This example describes the synthesis of the heterobifunctional monomer, N-(5-norborn-2-en-yl) maleimide, shown below:

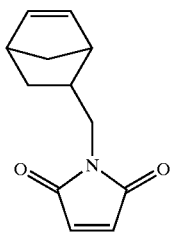

A. Preparation of 5-methylamino-norbornene. Allylamine (113 g, 1.98 mol) and dicyclopentadiene (DCPD) (65 g, 0.49 mol) were placed into an autoclave and heated to 220° C. for 24 hours. Excess allylamine was removed by distillation at atmospheric pressure. The 1:1 cyclopentadiene:allylamine Diels-Alder adduct was purified by vacuum distillation (55 g collected at 55–65° C. at 1 mm Hg). $^1$H and $^{13}$C NMR data were consistent with that expected for the 1:1 Diels-Alder adduct of cyclopentadiene and allylamine (see Sagane, *Makromol. Chemie*, 1993, 194, 37). Infrared spectroscopy confirmed the presence of the amino functional group.

B. Preparation of N-(5-norborn-2-en-yl) maleimide. Maleic anhydride (14.7 g, 0.150 mol) was dissolved in toluene (100 ml) in a two-neck round bottom flask. To this solution was slowly added $CH_3SO_3H$ (5.8 ml, 0.090 mol) followed by $NEt_3$ (12 mL, 0.087 mol). 5-methylamino-norbomene (17 g, 0.14 mol) was dissolved in toluene (15 ml) and added dropwise to the maleic anhydride solution over a 1 hour period. After amine addition was complete, the flask was equipped with a reflux condenser and a Dean-Stark trap and allowed to reflux for 16 hours. The toluene solution was washed with water, dried with $MgSO_4$, and the toluene was removed in vacuo to afford 20 g of a yellow solid. Infrared spectroscopy confirmed the presence of the maleimide group (1706 cm$^{-1}$, 825 cm$^{-1}$, 694 cm$^{-1}$) and $^1$H and $^{13}$C NMR spectroscopy were consistent with the formation of N-(5-norbornene-2-en-yl) maleimide.

EXAMPLE 2

Copolymerization of Norbornene and N-(5-norborn-2-en-yl)maleimide

N-(5-norbornene-2-en-yl) maleimide (1.0 g, 4.9 mmol) and norbomene were weighed into a 100 ml septum-capped vial equipped with a stir bar. The vial was purged with argon for 15 min and the vial was re-weighed to determine the actual amount of norbomene remaining in the vial, i.e., 0.78 g, 8.3 mmol (norbomene is volatile, therefore some of this monomer was lost during the argon purge). To the vial was added chlorobenzene (2 mL, chlorobenzene was dried over $CaH_2$ prior to use). The catalyst system, i.e., (allyl)PdCl (39 mg, 0.11 mmol) and AgSbF$_6$ (98 mg, 0.29 mmol) (see Risse, et. al., *Macromolecules*, 1996, 29, 2755) was weighed into a separate septum-capped vial and immediately purged with argon. After a 15 min purge, chlorobenzene (2 mL) was added to the catalyst mixture, and this mixture was allowed to stir at room temperature for 30 minutes. The catalyst solution was injected into the monomer solution using a syringe equipped with a 45 µm filter to remove the precipitated AgCl. The copolymerization mixture was allowed to stir at room temperature for 20 hrs. At this time, the viscosity of the solution had increased considerably. The solution was diluted with chlorobenzene (15 mL) and poured into a large excess of methanol (150 mL) to precipitate the copolymer and wash away any unreacted monomer and catalyst residues. The copolymer was isolated by filtration and dried in vacuo overnight at 70° C. to afford 700 mg (40% yield) of a white solid. Infrared spectroscopy confirmed the presence of the unreacted maleimide group, indicating polymerization had proceeded through the norbornene double bond only. $^1$H NMR spectroscopy further confirms the incorporation of the maleimide group into the copolymer (CDCl$_3$, δ 6.7, 2H, maleimido protons). Additionally, a differential scanning calorimetry analysis (DSC) was performed on the polymer revealing a large exotherm (peak at 323° C.), consistent with thermal crosslinking of the maleimide group.

EXAMPLE 3

Copolymerization of 5-n-butyl-norbornene and N-(5-norborn-2-en-yl)maleimide

N-(5-norbornene-2-en-yl) maleimide (44 g, 0.20 mol) and 5-n-butyl-norbomene (44 g, 0.30 mol) were weighed into a two-neck round bottom flask and immediately placed under an atmosphere of argon. Via cannula, 1-hexene (124 mL, 1.0 mol) was added as a chain transfer agent, followed by the reaction solvent $CH_2Cl_2$ (300 mL, dried over $CaH_2$ prior to use). The catalyst system, (allyl)PdCl (0.90 g, 2.5 mmol) and AgSbF$_6$ (2.3 g, 6.8 mmol) was prepared and introduced to the polymerization flask as described in Example 2. The polymerization was allowed to proceed for 48 hrs.

The polymerization solution was poured into a large excess of acetone (1 L) to precipitate the polymer and remove unreacted monomer and catalyst residues. The polymer was isolated by filtration and dried in vacuo at room temperature overnight. In this manner 48 g (55% yield) of a white solid was obtained. Infrared spectroscopy and $^1$H and $^{13}$C NMR spectroscopy confirmed the presence of the unreacted maleimide functional group, indicating polymerization had proceeded through the norbornenyl double bond only.

What is claimed is:

1. A heterobifunctional monomer of the following structure:

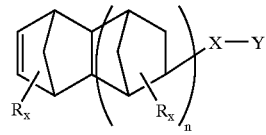

wherein:
each R is independently lower alkyl, —Br, or —I,
X is a covalent bond or a bridging group containing more than one carbon atom, selected from the group consisting of hydrocarbylene, substituted hydrocarbylene, heteroatom-containing hydrocarbylene, substituted heteroatom-containing hydrocarbylene, polysiloxane, polysiloxane-polyurethane block copolymer, and combinations of two or more thereof, optionally containing one or more linkers selected from the group consisting of a covalent bond, —O—, —S—, —NR—, —O—C(O)—, —O—C(O)—O—, —O—C(O)—NR—, —NR—C(O)—, —NR—C(O)—O—, —NR—C(O)—NR—, —S—C(O)—, —S—C(O)—O—, —S—C(O)—NR—, —S(O)—, —S(O)$_2$—, —O—S(O)$_2$—, —O—S(O)$_2$—O—, —O—S(O)$_2$—NR—, —O—S(O)—, —O—S(O)—O—, —O—S(O)—NR—, —O—NR—C(O)—, —O—NR—C(O)—O—, —O—NR—C(O)—NR—, —NR—O—C(O)—, —NR—O—C(O)—NR—, —NR—O—C(O)—O—, —NR—O—C(O)—NR—, —O—NR—C(S)—, —O—NR—C(S)—O—, —O—NR—C(S)—NR—, —NR—O—C(S)—, —NR—O—C(S)—O—, —NR—O—C(S)—NR—, —O—C(S)—, —O—C(S)—O—, —O—C(S)—NR—, —NR—C(S)—, —NR—C(S)—O—, —NR—C(S)—NR—, —S—S(O)$_2$—, —S—S(O)$_2$—O—, —S—S(O)$_2$—NR—, —NR—O—S(O)—, —NR—O—S(O)—O—, —NR—O—S(O)—NR—, —NR—O—S(O)$_2$—, —NR—O—S(O)$_2$—O—, —NR—O—S(O)$_2$—NR—, —O—NR—S(O)—, —O—NR—S(O)—O—, —O—NR—S(O)—NR—, —O—NR—S(O)$_2$—O—, —O—NR—S(O)$_2$—NR—, —O—NR—S(O)$_2$—, —O—P(O)R$_2$—, —S—P(O)R$_2$—, —NR—P(O)R$_2$—, wherein each R is independently hydrogen, alkyl or substituted alkyl, and combinations of any two or more thereof, Y is a maleimide, a nadimide, an itaconimide, an epoxy, a cyanate ester-substituted aryl, a propargyl-substituted aryl, an ethynyl-substituted aryl, a (meth)acrylate, an unsaturated anhydride, a vinyl ether, a vinyl ester, a divinyl compound, an allyl amide, a styrene, an oxazoline, or a benzoxazine, n is 0 to about 8, and each x is independently 0, 1, or 2.

2. The heterobifunctional monomer according to claim 1, wherein X is alkylene or oxy-alkylene comprising from 2 up to about 20 carbon atoms, arylene, or siloxane.

3. The heterobifunctional monomer according to claim 2, wherein X is alkylene comprising from 2 up to about 20 carbon atoms.

4. The heterobifunctional monomer according to claim 3, wherein the alkylene is $C_2$ to $C_6$ alkylene.

5. The heterobifunctional monomer according to claim 1, wherein Y is a maleimide, a nadimide, or an itaconimide.

6. The heterobifunctional monomer according to claim 1, wherein Y is a nadimide.

7. The heterobifunctional monomer according to claim 6, wherein the nadimide is substituted with 1 or 2 independently selected lower alkyl, —Br, or —I.

8. The heterobifunctional monomer according to claim 1, wherein Y is an itaconimide.

9. The heterobifunctional monomer according to claim 8, wherein the itaconimide is substituted with 1 or 2 independently selected lower alkyl, —Br, or —I.

10. A method for synthesizing heterobifunctional monomers according to claim 1, the method comprising contacting a primary amine with a defined reactant under cyclodehydration reaction conditions, thereby producing the desired heterobifunctional monomer, wherein:
the primary amine has the structure:

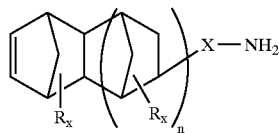

each R is independently lower alkyl, —Br, or —I,
X is a covalent bond or a bridging group containing more than one carbon atom,
n is 0 to about 8, and
each x is independently 0, 1, or 2; and
the defined reactant is selected from optionally substituted maleic anhydride, a Diels-Alder adduct of maleic anhydride and cyclopentadiene, a methylene-dihydro-furan-2,5-dione, or an epoxy.

11. A heterobifunctional monomer of the following structure:

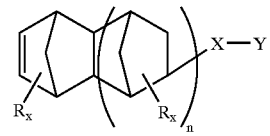

wherein:
each R is independently lower alkyl, —Br, or —I,
X is an optional bridging group,
Y is a nadimide, an itaconimide, a (meth)acrylate, an unsaturated anhydride, a vinyl ether, a vinyl ester, a divinyl compound, an allyl amide or, a styrene,
n is 0 to about 8, and
each x is independently 0, 1, or 2.

12. A heterobifunctional monomer of the following structure:

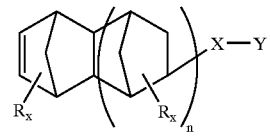

wherein:
each R is independently hydrogen, lower alkyl, —Br, or —I,
X is an optional bridging group,
Y is a nadimide, an itaconimide, a (meth)acrylate, an unsaturated anhydride, a vinyl ether, a vinyl ester, a divinyl compound, an allyl amide, or a styrene, n is 0 or 2 to about 8, and
each x is independently 0, 1, or 2.

13. A polymer comprising a plurality of heterobifunctional monomers according to claim 1.

14. The polymer according to claim 13, wherein the norbornyl functional groups of the heterobifunctional monomers are polymerized.

15. The polymer according to claim 13, wherein the Y functional groups of the heterobifunctional monomers are polymerized.

16. The polymer according to claim 13, wherein norbornyl functional groups of the heterobifunctional monomers are alternately polymerized with the Y functional groups of the heterobifunctional monomers.

17. A block copolymer comprising:
(a) one or more blocks of a plurality of polymerized heterobifunctional monomers according to claim 1, and
(b) one or more blocks of a polymerized comonomer selected from the group consisting of the heterobifunctional monomer, a maleimide, a nadimide, an itaconimide, an epoxy, a cyanate ester-substituted aryl, a propargyl-substituted aryl, an ethynyl-substituted aryl, a (meth)acrylate, an unsaturated anhydride, a vinyl ether, a divinyl compound, an allyl amide, a styrene, an oxazoline, or a benzoxazine, wherein the block(s) of (a) are different from the block(s) of (b).

18. A polymer having the structure:

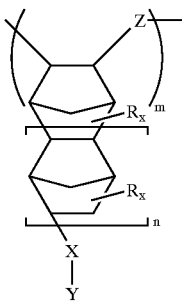

wherein:
each R is independently lower alkyl, —Br, or —I,
X is an optional bridging group,
Y is a nadimide, an itaconimide, a (meth)acrylate, an unsaturated anhydride, a vinyl ether, a vinyl ester, a divinyl compound, an allyl amide, or a styrene, each Z is optionally present, and when present, is independently derived from any cationically polymerizable monomer, any free-radically polymerizable monomer, or any coordinatively polymerizable monomer,
m is in the range of about 3 up to about 10,000,
n is 0 to about 8, and
x is 0 up to 2.

19. A polymer according to claim 18, wherein X is alkylene or oxyalkylene comprising up to about 20 carbon atoms, arylene, or siloxane.

20. A polymer having the structure:

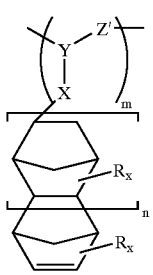

wherein:
each R is independently hydrogen, lower alkyl, —Br, or —I,
X is an optional bridging group,
Y is a nadimide, an itaconimide, a (meth)acrylate, an unsaturated anhydride, a vinyl ether, a vinyl ester, a divinyl compound, an allyl amide, or a styrene,
each Z' is optionally present, and when present, is independently derived from any cationically polymerizable monomer, any anionically polymerizable monomer, any free-radically polymerizable monomer, or any coordinatively polymerizable monomer,
m is in the range of about 3 up to about 10,000,
n is 0 to about 8, and
x is 0 up to 2.

21. A polymer according to claim 20, wherein X is an alkylene or oxyalkylene comprising up to about 20 carbon atoms, an arylene, or a siloxane.

22. A method for synthesizing a polymer according to claim 13, the method comprising subjecting a plurality of the heterobifunctional monomers to a Zeigler-type coordinative reaction, a cationic cure, an anionic cure, a free radical ring opening or a ring-opening metathesis reaction.

23. A method for synthesizing a polymer according to claim 14, the method comprising subjecting a plurality of the heterobifunctional monomers to a Zeigler-type coordinative reaction, a cationic cure, or a free radical ring opening.

24. A method for synthesizing a polymer according to claim 15, the method comprising subjecting a plurality of the heterobifunctional monomers to an anionic cure.

25. A method for synthesizing a polymer according to claim 16, the method comprising subjecting a plurality of the heterobifunctional monomers to a free radical cure.

26. A method for synthesizing a polymer according to claim 17, the method comprising
(a) synthesizing a first block polymer by subjecting a first plurality of the heterobifunctional monomers to a Zeigler-type coordinative reaction, a cationic cure, or a free radical ring opening,
(b) synthesizing a second block polymer by subjecting a second plurality of heterobifunctional monomers to a free radical reaction, an anionic cure, or a UV catalyzed cationic cure, and
(c) subjecting a plurality of first and second block polymers to one or more of a Zeigler-type coordinative reaction, a cationic cure, an anionic cure or a ring-opening metathesis reaction.

27. A method for synthesizing a polymer according to claim 18, the method comprising subjecting a heterobifunctional monomer of claim 1 and a plurality of monomers Z to one or more of a Zeigler-type coordinative reaction, a cationic cure, an anionic cure, a free radical ring opening or a ring-opening metathesis reaction.

28. A method for synthesizing a polymer having the structure:

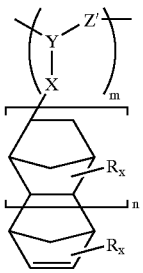

wherein:
each R is independently hydrogen, lower alkyl, —Br, or —I,
X is an optional bridging group,
Y is a nadimide, an itaconimide, a (meth)acrylate, an unsaturated anhydride, a vinyl ether, a vinyl ester, a divinyl compound, an allyl amide, or a styrene,
each Z' is optionally present, and when present, is independently derived from any cationically polymerizable monomer, any anionically polymerizable monomer, any free-radically polymerizable monomer, or any coordinatively polymerizable monomer,
m is in the range of about 3 up to about 10,000,
n is 0 to about 8, and
x is 0 up to 2, the method comprising subjecting a heterobifunctional monomer of claim 1 and a plurality of monomers Z' to one or more of a Zeigler-type coordinative reaction, a cationic cure, an anionic cure, a free radical ring opening or a ring-opening metathesis reaction.

29. A thermoset resin comprising a polymer according to claim 13.

30. A thermoset resin comprising a polymer according to claim 14.

31. A thermoset resin comprising a polymer according to claim 15.

32. A thermoset resin comprising a polymer according to claim 16.

33. A thermoset resin comprising a polymer according to claim 17.

34. A thermoset resin comprising a polymer according to claim 18.

35. A thermoset resin comprising a polymer according to claim 20.

36. A thermosetting resin composition comprising:

(a) a heterobifunctional monomer according to claim 1;

(b) in the range of 0.2 up to 5 wt % of at least one curing catalyst, based on the total weight of the composition (c) optionally, at least one hydrophobic cyanate ester monomer, and (d) optionally, at least one polycyclic olefin having at least one terminal norbornene functional group;

(e) optionally, at least one of a maleimide, a nadimide, or an itaconimide having, respectively the formulas XIII, XIV, and XV:

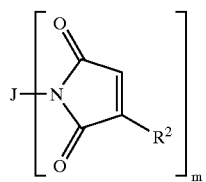

(XIII)

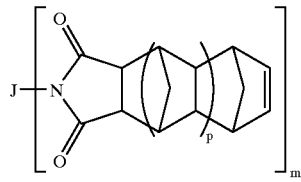

(XIV)

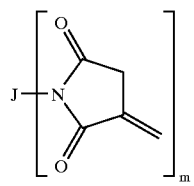

(XV)

wherein:

m=1–15, p=0–15, each $R^2$ is independently selected from hydrogen or lower alkyl, and J is a monovalent or a polyvalent moiety comprising organic or organosiloxane radicals, and combinations of two or more thereof.

37. An assembly comprising a first article permanently adhered to a second article by a cured aliquot of the thermosetting resin composition according to claim 36.

38. An assembly according to claim 37, wherein the first article and the second article are separate layers of a laminated circuit board.

39. An article comprising a circuit board having a solder mask deposited thereon, wherein the solder mask is prepared from the composition according to claim 36.

40. An article comprising an electronic component encased within an aliquot of composition according to claim 36.

41. A polymer comprising a plurality of norbornyl-containing heterobifunctional monomers, wherein the polymer has one or more performance properties which render it suitable for use in the manufacture of electronic components, and wherein the performance properties are selected from the group consisting of excellent moisture resistance, excellent ionic purity, low dielectric constant, good thermal properties, hydrophobic, high Tg, and low coefficient of thermal expansion.

* * * * *

UNITED STATES PATENT AND TRADEMARK OFFICE
CERTIFICATE OF CORRECTION

PATENT NO. : 6,946,523 B2
APPLICATION NO. : 10/612545
DATED : September 20, 2005
INVENTOR(S) : S. Dershem et al.

Page 1 of 1

It is certified that error appears in the above-identified patent and that said Letters Patent is hereby corrected as shown below:

Title page
Item (57) Abstract, line 2, delete "users" and insert -- uses --.

Column 6, Structure (V), delete "-$(CR"_2)_r$-$((O-)_q$-$(CR"_2)_s)$-" and insert
-- -$(CR"_2)_r$-$[(O-)_q$-$(CR"_2)_s]$- --.

Column 14
Line 18, delete "SII'" and insert -- SII --.
Line 25, delete "yams" and insert -- yarns --.

Column 16
Line 2, delete "-S(O)" and insert -- -S(O)- --.

Column 22
Line 15, delete "N-(5-norbornene-2-en-yl)" and insert -- N-(5-norborn-2-en-yl) --.
Line 17, delete "norbomene" and insert -- norbornene --.
Line 61, delete "-$S(O)_2$" and insert -- -$S(O)_2$- --.

Signed and Sealed this

Thirteenth Day of May, 2008

JON W. DUDAS
*Director of the United States Patent and Trademark Office*